United States Patent [19]

Toyoda et al.

[11] Patent Number: 4,555,583

[45] Date of Patent: Nov. 26, 1985

[54] PREPARATION PROCESS FOR GLYOXAL

[75] Inventors: Yoshiaki Toyoda, Takaishi; Kazuo Wakimura, Sennan; Tadaharu Hase; Nobumasa Arashiba, both of Takaishi, all of Japan

[73] Assignee: Mitsui Toatsu Chemicals, Incorporated, Tokyo, Japan

[21] Appl. No.: 597,067

[22] PCT Filed: Aug. 30, 1983

[86] PCT No.: PCT/JP83/00283

§ 371 Date: Mar. 28, 1984

§ 102(e) Date: Mar. 28, 1984

[87] PCT Pub. No.: WO84/00955

PCT Pub. Date: Mar. 15, 1984

[30] Foreign Application Priority Data

Aug. 30, 1982 [JP] Japan .................. 57-149351
Aug. 31, 1982 [JP] Japan .................. 57-150082

[51] Int. Cl.$^4$ ............................................ C07C 45/29
[52] U.S. Cl. ..................................... 568/473; 568/471
[58] Field of Search .................. 568/471, 472, 473

[56] References Cited

U.S. PATENT DOCUMENTS

| 3,948,997 | 4/1976 | Howe et al. | 568/473 |
| 4,242,282 | 10/1982 | Diem et al. | 568/473 |
| 4,258,216 | 3/1981 | Trecek | 568/473 |
| 4,302,609 | 11/1981 | Baltes et al. | 568/473 |

FOREIGN PATENT DOCUMENTS

| 1064963 | 10/1923 | Canada | 568/473 |
| 2634439 | 10/1977 | Fed. Rep. of Germany | 568/473 |
| 38227 | 3/1983 | Japan | 568/473 |
| 59933 | 4/1983 | Japan | 568/473 |
| 1272592 | 5/1972 | United Kingdom | 568/473 |

*Primary Examiner*—Werren B. Lone
*Attorney, Agent, or Firm*—Fisher, Christen & Sabol

[57] ABSTRACT

Glyoxal may be produced with a high yield by bringing a gas, which has been formed by diluting ethylene glycol and molecular oxygen with an inert gas, into contact at a high temperature with a silver catalyst in the simultaneous presence of phosphorus or a phosphorus compound so as to effect the gas phase oxidation of the ethylene glycol.

In the above process, it is possible to suppress the formation of glycolaldehyde, a reaction intermediate, and also to enhance the stability of the reaction by using silver powder having particle sizes of $1 \times 10^{-3}$ mm or smaller as at least part of the silver catalyst.

8 Claims, No Drawings

PREPARATION PROCESS FOR GLYOXAL

TECHNICAL FIELD

This invention relates to a process for preparing glyoxal by the gas phase oxidation of ethylene glycol.

BACKGROUND ART

As preparation process for glyoxal, there have generally been known processes relying upon the oxidation of acetylene or ethylene, the oxidation of acetaldehyde with nitric acid, the oxidation of ethylene glycol, and the like. However, the process relying upon the oxidation of acetaldehyde with nitric acid is mainly employed in the industry.

The oxidation of acetaldehyde with nitric acid requires, as an oxidizing agent, nitric acid in an amount at least equal by mole to the acetaldehyde to be reacted. It is thus accompanied by such shortcomings that unreacted nitric acid is unavoidably mixed and organic acids are by-produced as impurities in relatively large amounts, thereby making a complicated separation and purification step indispensable.

On the other hand, a number of proposals have been made for the process for preparing glyoxal by oxidizing ethylene glycol. There are, for example, a process for effecting the oxidation with oxygen by using an oxidizing catalyst which is made of copper and/or silver and phosphorus (Japanese Patent Publication No. 1364/1973) and an oxidation process which is carried out, in the presence of a catalyst containing phosphorus and copper, phosphorus and silver, or phosphorus, copper and silver, by incorporating a bromine compound within an amount which does not lower the conversion of ethylene glycol to about 90% or less in the mixed feed gas (Japanese Patent Laid-open No. 17408/1977). It has also been proposed to use a copper-containing catalyst (U.S. Pat. No. 2,339,282) and to effect the oxidation in the simultaneous presence of a copper-containing catalyst and a halogen compound in a cylindrical reactor made of a Cu-Si-Mn alloy. However, the above processes which employ these alloy-based catalysts were not significantly advantageous from the industrial viewpoint, since the preparations of the catalysts were difficult, their service life in which they can maintain reaction results at high levels was short, and the regeneration treatments of the catalysts were complicated.

As processes relying upon the oxidation of ethylene glycol, it has also been proposed to effect the oxidation in the presence of silver crystals having uniform particle sizes (0.1-2.5 mm)—Japanese Patent Laid-open No. 103809/1979—and to carry out the oxidation by using a copper-containing catalyst and in the simultaneous presence of a phosphorus compound which is vaporized under reaction conditions (Japanese Patent Laid-open No. 55129/1980). The yields of glyoxal by these processes were not significantly high and these processes are not satisfactory as industrial preparation processes.

However, the preparation process for glyoxal relying upon the gas phase oxidation of ethylene glycol has by itself been considered to be an advantageous process from the standpoint of economy because it uses, as a raw material source, ethylene glycol which is a derivative of ethylene oxide obtained from inexpensive natural gas as its starting raw material and is thus economically superior compared with the oxidation of acetaldehyde with nitric acid.

DISCLOSURE OF THE INVENTION

An object of this invention is to provide a process for preparing glyoxal with a high yield by the gas phase oxidation of ethylene glycol.

Another object of this invention is to provide a preparation process for glyoxal, which features very little formation of glycol aldehyde as a reaction intermediate, is easy to separate and purify the intended product and is thus suitable as an industrial preparation process.

The above and other objects can be achieved by the present invention which will next be defined. Namely, the present invention relates to a process for preparing glyoxal by subjecting ethylene glycol to gas-phase oxidation, which process comprises bringing the ethylene glycol and a gas containing molecular oxygen into contact at a high temperature with a silver catalyst in the simultaneous presence of phosphorus or a phosphorus compound to effect the oxidation of the ethylene glycol.

The formation of glycol aldehyde as a reaction intermediate can be sharply lowered and the stability of the reaction can be improved especially by using, as at least part of the above-described silver catalyst, fine silver powder having particle sizes of $1 \times 10^{-3}$ mm or smaller.

BEST MODE FOR CARRYING OUT THE INVENTION

In the present invention, the phosphorus or phosphorus compound may be provided for the reaction by mixing a predetermined amount of phosphorus or a phosphorus compound in ethylene glycol in advance. Alternatively, it may be added to the reaction system either as is or as a solution, separately from the ethylene glycol. As phosphorus compounds effectively useful in the present invention, may be mentioned inorganic phosphorus compounds such as ammonium orthophosphate, diammonium hydrogenphosphate, ammonium dihydrogenorthophosphate and ammonium dihydrogenphosphite as well as a variety of organic phosphorus compounds including primary to tertiary phosphines such as mono-, di- and trimethylphosphines, phosphorous esters such as methyl phosphite and ethyl phosphite, dimethyl methylphosphonate, and diethyl ethylphosphonate. However, it is not preferred to use a phosphorus compound having a high boiling point because it necessitates raising the temperature of an evaporator to a particularly high level, or it remains in the evaporator and builds up there in decomposed forms, thereby causing the apparatus material to undergo corrosion and permitting the resultant iron rust and the like to reach the reaction layer so that the reaction may be affected deleteriously. More preferably, an organic phosphorus compound having a relatively low boiling point such as, for example, methyl phosphite, ethyl phosphite, methyl phosphate or ethyl phosphate is used accordingly.

It is suitable to add the phosphorus or a phosphorus compound in an amount in the range of 1–50 ppm as calculated in terms of phosphorus based on the ethylene glycol. The addition of phosphorus or a phosphorus compound suppresses to a significant extent the formation of oxidation products such as carbon monoxide and carbon dioxide and decomposition products such as formaldehyde and considerably improves the yield of glyoxal, the intended product. The proportion of produced carbon monoxide, carbon dioxide or formaldehyde increases immediately even if the addition of phosphorus or a phosphorus compound is briefly stopped. Thus, this indicates that the thus-added phosphorus or phosphorus compound is not acting in a state deposited on the catalyst but is acting effectively in the gas phase.

When the phosphorus or a phosphorus compound is added in any amount in excess of 50 ppm as calculated in terms of phosphorus, the amount of produced glycolaldehyde which is the reaction intermediate increases and, in addition, the conversion of ethylene glycol decreases and more unreacted ethylene glycol remains. Therefore, it is not preferred to add the phosphorus or a phosphorus compound in such amounts. However, the effects of the phosphorus or a phosphorus compound cannot be drawn out to any sufficient extent and the objects of the present invention cannot be fulfilled, if the phosphorus or a phosphorus compound is incorporated in any amounts lower than 1 ppm. As retarding agents against such a silver-base catalytic system, the above referred-to Japanese Patent Laid-open No. 103809/1979 discloses by way of examples halogenated hydrocarbons, halogens and hydrogen halides. Compared with such retarding agents, the effects which have been brought about by the addition of phosphorus or a phosphorus compound in accordance with the present invention are remarkable. In view of the still-improved high yield of glyoxal, the process of this invention is very meritorious as an industrial preparation process.

Turning next to the catalyst, it is feasible to use silver of any type regardless of its preparation process or method, including, for example, silver crystals obtained by the electrolysis method and having particle sizes of 0.1–2.5 mm; fine silver powder having particle sizes of $1 \times 10^{-3}$ mm and smaller, for example, fine silver powder produced chemically, e.g., by the alkaline precipitation method; fine silver powder obtained in accordance with the so-called gas evaporation method, namely, by conducting a variety of heating methods in an inert gas; or fine silver powder obtained by the vacuum evaporation method; or the like. In the case of a fine powdery silver catalyst, it may be used solely or in combination with crystalline silver grains having grain sizes of 0.1 mm or larger.

The process of this invention can be conducted by passing a gas, which contains the raw materials, i.e., ethylene glycol and oxygen, as a downward current through a layer of the silver catalyst. Where a silver catalyst having relatively large grain sizes is used to form the layer of silver catalyst, it is preferred to pack the silver catalyst in at least three layers in accordance with grain size. It is preferred, for example, to change the grain size distribution in such a way that the silver grains become coarser in the direction from the top to the bottom, for example, by packing 10–30 wt. % of silver grains having grain sizes of 0.1–0.35 mm in the uppermost layer, 35–65 wt. % of silver grains having grain sizes of 0.35–0.85 in the next layer and 5–55 wt. % of silver grains having grain sizes of 0.85–2.5 mm in the lowermost layer. The number of layers may, of course, be increased further. Where fine silver powder having particle sizes of $1 \times 10^{-3}$ mm and smaller is used as the silver catalyst and the reaction gas flows, for example, as a downward current through the reactor, it may be mentioned as one example of a practical application method to lay crystalline silver particles having particle sizes of about 0.1 mm and larger over a copper-made wire net of a suitable mesh and then to pack a fine powdery silver catalyst having particle sizes of $1 \times 10^{-3}$ mm and smaller on the crystalline silver particles so that the fine powdery silver catalyst may be protected from the scattering loss. It is also feasible to use, in place of silver grains having grain sizes of about 0.1 mm and greater, an inert carrier having a small specific surface area such as α-alumina or steatite balls. However, such an inert carrier brings about somewhat poorer reaction results compared with silver grains or particles. This can be attributed to the good thermal conductivity of silver. A copper-made wire net is used as mentioned above but it is not feasible to use a wire net made of iron or the like which serves as a catalyst poison. Needless to say, silver particles or grains having different particle or grain sizes may also be used as long as they are combined with at least fine silver powder having particle sizes of $1 \times 10^{-3}$ mm and smaller.

The combined use of the trace amount of phosphorus or phosphorus compound and the fine powdery silver catalyst, especially having particle sizes of $1 \times 10^{-3}$ mm and smaller, has synergistically combined the meritorious features of both phosphorus or a phosphorus compound and a silver catalyst and has hence brought about outstanding effects, although the merits and demerits of the action exhibited by the phosphorus or phosphorus compound per se and those shown by the fine powdery silver catalyst per se are mutually contradictory.

In other words, when the amount of the phosphorus compound is increased without employing the fine powdery silver catalyst, the amounts of produced carbon dioxide, carbon monoxide and formaldehyde decrease and the glyoxal selectivity is improved but glycolaldehyde, which is the reaction intermediate, and unreacted ethylene glycol increase. In the absence of phosphorus or a phosphorus compound, on the other hand, the reaction results vary depending on the particle or grain sizes of the silver catalyst to be used. Where the above-mentioned fine silver powder having particle sizes of $1 \times 10^{-3}$ mm and smaller are used as at least part of the catalyst to effect the gas phase oxidation of ethylene glycol instead of using silver crystals having grain sizes of about 0.1 mm and greater as the catalyst, the silver powder has remarkably high oxidation activity but is accompanied by a greater occurrence of decomposition and oxidation products such as carbon monoxide and carbon dioxide. Therefore, the silver powder cannot make the yield of the intended compound, glyoxal, significantly better than the silver crystals.

In the presence of both phosphorus or a phosphorus compound and a fine powdery silver catalyst as opposed to the above description, the increment of glycolaldehyde and unreacted ethylene glycol is considerably suppressed and the glyoxal selectivity is improved.

In the sole presence of a crystalline silver catalyst having grain sizes of about 0.1 mm and greater, it is preferred, as described above, that the phosphorus or a phorphorus compound be present in an amount of 1–50 ppm as calculated in terms of phosphorus based on the ethylene glycol. As the amount of the phosphorus or a phosphorus compound increases, the amounts of decomposition and oxidation products such as carbon dioxide, carbon monoxide and formaldehyde decrease and the glyoxal selectivity is improved but the unreacted ethylene glycol and glycolaldehyde, the reaction intermediate, tend to increase. In addition, the reaction deactivating phenomenon is induced to occur and the continuity and stability of the reaction are liable to be impaired due to a reduction in reaction temperature. Where fine silver powder having particle sizes of $1 \times 10^{-3}$ mm and smaller is used as at least part of the catalyst, it especially improves the reaction stability to a significant extent and remarkably suppresses the occurrence of unreacted ethylene glycol and glycolaldehyde which is the reaction intermediate. Even if a catalyst of the above particle sizes is used, the addition of phosphorus or a phosphorus compound in an amount exceeding 50 ppm as calculated in terms of phosphorus induces a variety of reaction-retarding actions to occur to such an extent that the reaction may not be continued any further. Thus, it is not practical to use phosphorus or a phosphorus compound in such an excess amount.

In the process of this invention, it is preferred to use the molecular oxygen at a proportion of 0.7–2.0 moles per mole of ethylene glycol. If oxygen is present in excess of 2 moles, oxidation products such as carbon dioxide and carbon monoxide and a decomposition product such as formaldehyde are remarkably increased and the yield of glyoxal is lowered. If oxygen is present in any amount less than 0.7 mole, the above oxidation products are decreased but more unreacted ethylene glycol is caused to remain. Thus, it is not preferred economically to use oxygen at such a low level. Furthermore, such a low oxygen level leads to a reduction in reaction temperature and makes it difficult for the stable reaction to proceed further. Therefore, it is not practical to use oxygen at such a low level. As molecular oxygen, either pure oxygen or air may be used. The latter is, however, preferred from the standpoint of economy.

In the present invention, it is preferred to conduct the reaction by diluting ethylene glycol and molecular oxygen with an inert gas so that glyoxal can be obtained with a high yield. As the inert gas, as well known in the art, may be employed nitrogen, a rare gas such as helium or argon, carbon dioxide or steam. The exhaust gas of the reaction may also be recirculated for use as the diluting gas. When effecting the dilution with the inert gas, at least 5 moles of the latter gas may be mixed with each mole of ethylene glycol. If the inert gas is used in any amount less than 5 moles, oxidation products such as carbon dioxide and carbon monoxide are increased and the yield of glyoxal is thus decreased.

The gas phase oxidation in the process of this invention is suitably carried out at a reaction temperature in the range of 450°–650° C. Any reaction temperature lower than 450° C. results in an excessively low conversion of ethylene glycol, thereby necessitating separating and recovering a great deal of unreacted ethylene glycol and recirculating it. Such excessively low reaction temperatures also lead to a greater occurrence of glycolaldehyde. If the reaction temperature exceeds 650° C. on the other hand, more carbon dioxide and carbon monoxide are produced as oxidation products. Accordingly, such an excessively high reaction temperature is not preferred.

It is preferred that the residence time of the reaction gas in the silver catalyst layer not exceed 0.03 second. If the residence time is longer than the aforementioned time period, oxidation products such as carbon dioxide and carbon monoxide and decomposition products such as formaldehyde are increased.

It is necessary to cool the reaction product gas as soon as possible after it has passed out of the catalyst layer. It is not preferred to allow the reaction gas to stay for a long time period in the high-temperature zone because the decomposition of glyoxal and the like are promoted. The thus-cooled gas is subjected to partial condensation as needed, in order to recover unreacted ethylene glycol. Where the reaction gas does not contain unreacted ethylene glycol or contains ethylene glycol at such trace concentrations that it does not cause any problem in the final glyoxal and it is thus unnecessary to go to the trouble of removing ethylene glycol from the reaction gas, the reaction gas is cooled and condensed in a heat exchanger and the resultant glyoxal is then separated from the remaining gaseous components in accordance with the usual absorption procedure which makes use of water.

The thus-obtained aqueous glyoxal solution contains organic acids and a trace amount of formaldehyde as impurities. The formaldehyde is readily removed by the usual stripping operation in which steam is blown in the aqueous glyoxal solution. In the course of the stripping operation, parts of organic acids having low boiling points such as formic acid and acetic acid are also removed. An aqueous glyoxal solution obtained by the oxidation of ethylene glycol in the presence of a fine powdery silver catalyst hardly contains the reaction intermediate, glycolaldehyde, at all compared with that synthesized without the fine powdery silver catalyst. In addition, an aqueous glyoxal solution which has been subjected to the formaldehyde stripping treatment contains organic acids at such a total acid concentration that it is suitable to maintain the stability of the product. Accordingly, it is unnecessary to subject the aqueous glyoxal solution to any further separation treatment. It is thus sufficient to apply only a decolorization treatment and/or a treatment with a cation exchange resin as needed.

In this regard, the gaseous components which have been removed before may be exhausted as an exhaust gas or may partially be recirculated as an inert gas for reutilization.

In the process of the present invention, it is possible as mentioned above to prepare glyoxal with a high yield from ethylene glycol while suppressing the occurrence of by-products. In addition, the process of this invention features the excellent stability of the gas phase oxidation. Furthermore, the process of this invention has a further merit that the separation and purification steps of the reaction product can be simplified.

The present invention will hereinafter be described in further detail by the following Examples:

COMPARATIVE EXAMPLE 1

Seventeen g of silver grains obtained by the electrolysis of an aqueous silver nitrate solution and having grain sizes of 0.84–1.5 mm were laid in the lowermost layer of a reactor, followed by 10 g of silver grains obtained in the same manner and having grain sizes of 0.35–0.84 mm over the first-mentioned silver grains, 8 g of silver grains obtained in the same manner and having grain sizes of 0.16–0.35 mm over the second-mentioned silver grains, and 1.0 g of fine powdery silver obtained by the vacuum deposition method and having an average particle size of about $7 \times 10^{-5}$ mm as the uppermost layer. The overall height of the packed layer was about 30 mm.

Into the thus-prepared reactor, ethylene glycol, steam, air and nitrogen were charged through a preheater at 162 g/hr, 162 g/hr, 280 liters/hr and. 800 liters/hr, respectively, as a downward current. They were reacted at a reaction temperature of 521° C. After cooling the reaction gas, reaction products were separated and collected in an absorption tower which employed water as its absorbent.

As a result, the conversion of ethylene glycol was 100% and the glyoxal selectivity and formaldehyde selectivity were 44.3% and 12.4%, respectively.

EXAMPLE 1

A reaction was carried out in the same reactor and under the same conditions as those used in Comparative Example 1 except that 26.8 ppm of triethyl phosphite (5 ppm as calculated in terms of phosphorus), based on the feed ethylene glycol, was added. The reaction temperature was lowered to 502° C.

The reaction resulted in a conversion of ethylene glycol of 100%, a glyoxal selectivity of 80.1% and a formaldehyde selectivity of 2.1%. Glycolaldehyde, which is the reaction intermediate, was produced in a trace amount.

COMPARATIVE EXAMPLE 2

Thirty-eight grams of a granular silver catalyst, which had been obtained by the electrolysis of an aqueous silver nitrate solution, were packed in a reactor by first laying 20 g of silver grains having grain sizes of 0.84–1.5 mm and obtained by classification as a lowermost layer, then 10 g of silver grains having grain sizes of 0.35–0.84 mm and obtained in the same manner over the first-mentioned silver grains, and finally 8 g of silver grains having grain sizes of 0.16–0.35 mm and obtained in the same manner as an uppermost layer. The overall height of the packed layer was about 30 mm.

A feed gas having the same composition as that of Comparative Example 1 was caused to pass through the above-prepared reactor without the addition of triethyl phosphite under the same conditions as in Comparative Example 1 except that the reaction temperature was set at 510° C. The conversion of ethylene glycol, glyoxal selectivity and formaldehyde selectivity were 100%, 53% and 5.2%, respectively.

EXAMPLE 2

A reaction was carried out under the same conditions as in Comparative Example 2 except that 26.8 ppm of triethyl phosphite (5 ppm as calculated in terms of phosphorus), based on the ethylene glycol, was added and the reaction temperature was set at 501° C.

The conversion of ethylene glycol, glyoxal selectivity and formladehyde selectively were 100%, 80.4% and 2.5%, respectively, but the reaction intermediate, glycolaldehyde, was also by-produced at a rate of 1.3% in terms of selectivity.

COMPARATIVE EXAMPLE 3

In the reaction of Example 2, the addition of triethyl phosphite was stopped and, upon an elapsed time of 10 minutes after the stoppage of the triethyl phosphite addition, reaction products were separated and collected and then subjected to analysis. The reaction temperature went up to 509° C. The conversion of ethylene glycol, glyoxal selectivity and formaldehyde selectivity were 100%, 53.5% and 5.4%,respectively. The formation of glycolaldehyde was not observed.

EXAMPLE 3

A reaction was carried out at 496° C. under the same reaction conditions as in Comparative Example 2 except that 53.6 ppm of triethyl phosphite (10 ppm calculated in terms of phosphorus), based on the ethylene glycol, was added.

The conversion of ethylene glycol, glyoxal selectivity and formaldehyde selectivity were 98.9%, 84.6% and 1.0%, respectively. It was observed that the yield of glyoxal was improved owing to the increment in the added phosphorus compound. On the other hand, it was also found that the reaction temperature tended to vary as the feeding rates of the raw materials changed.

EXAMPLE 4

A reaction was carried out under the same reaction conditions as in Example 1 except that 53.6 ppm of triethyl phosphite (10 ppm as calculated in terms of phosphorus), based on the ethylene glycol, was added and the reaction temperature was set at 497° C.

The conversion of ethylene glycol, glyoxal selectivity and formaldehyde selectivity were 99.9%, 84.1% and 0.9% respectively. This reaction result exhibits the improved effects of the combined addition of the fine powdery silver catalyst and phosphorus compound in that there is little formation of by-products and the selectivity of the intended product, glyoxal, is extremely high. In the operation performance, the reaction temperature did not vary and excellent stability was observed, unlike Example 3.

EXAMPLE 5

Thirty-nine grams of silver nitrate were dissolved in 140 ml of pure water, followed by a gradual dropwise addition with stirring of an aqueous solution which had been prepared by dissolving 20 g of NaOH in 30 ml of pure water. The resultant brownish precipitate was collected by suction filtration and washed well with pure water. The precipitate was then suspended in 180 ml of pure water, to which 12 ml of a 30% aqueous solution of formaldehyde was added while stirring the suspension vigorously. At the same time, an aqueous 5-N NaOH solution was added to maintain the pH of the suspension within 8–12. The resultant mixture was then stirred for 30 minutes and then allowed to stand. The thus-formed gray precipitate was collected by suction filtration and washed thoroughly with pure water. It was then dried at 110° C. Twenty-five grams of silver having an average particle size of about 0.25 $\mu$m (2500 Å) were obtained.

In a reactor, 17.5 g of silver grains similar to those employed in Example 1, obtained by the electrolysis of an aqueous silver nitrate solution and having grain sizes of 0.84–1.5 mm, was spread as a lowermost layer. Laid successively over the lowermost layer were 10 g of silver grains obtained in the same manner and having grain sizes of 0.35–0.84 mm, 8 g of silver grains obtained in the same manner and having grain sizes of 0.16–0.35 mm, and finally 1.0 g of the fine silver powder obtained above in accordance with the alkaline precipitation method. The overall height of the packed layer was about 30 mm.

A reaction was conducted at 501° C. in the same manner as in Example 1, by adding 26.8 ppm of triethyl phosphite (5 ppm as calculated in terms of phosphorus) based on the ethylene glycol. As a result, the conversion of ethylene glycol, glyoxal selectivity and formaldehyde selectivity were 100%, 81.0% and 2.3%, respectively, and the occurrence of the reaction intermediate, glycolaldehyde, was limited to a trace amount.

COMPARATIVE EXAMPLE 4

A reaction was carried out in the same manner as in Example 2 except that 50 ppm of ethylene dichloride (35.8 ppm as chlorine), based on the ethylene glycol, was added instead of triethyl phosphite and the reaction temperature was set at 498° C.

As a result, the conversion of ethylene glycol, glyoxal selectivity and glycolaldehyde selectivity were 100%, 60.8% and 5.6%, respectively.

COMPARATIVE EXAMPLE 5

A reaction was carried out in the same manner as in Example 2 except that 50 ppm of bromoform (47 ppm as bromine), based on the ethylene glycol, was added in place of triethyl phosphite and the reaction temperature was set at 505° C.

As a result, the conversion of ethylene glycol, glyoxal selectivity and glycolaldehyde selectivity were 100%, 62.1% and 6.3%, respectively.

EXAMPLE 6

A reaction was effected in the same manner as in Example 2 except that 22.7 ppm of trimethyl phosphate (5 ppm as calculated in terms of phosphorus), based on the ethylene glycol, was added and the reaction temperature was set at 497° C.

As a result, the conversion of ethylene glycol, glyoxal selectivity and glycolaldehyde selectivity were 99.0%, 78.6% and 2.3%, respectively.

EXAMPLE 7

A reaction was carried out in the same manner as in Example 2 except that 36.2 ppm of $(C_2H_5O)_2POCH_2COOC_2H_5$ (5 ppm as calculated in terms of phosphorus), based on the ethylene glycol, was added and the reaction temperature was set at 500° C.

As a result, the conversion of ethylene glycol, glyoxal selectivity and glycolaldehyde selectivity were 99.9%, 81.0% and 3.2%, respectively.

EXAMPLE 8

A reaction was carried out in the same manner as in Example 2 except that 12.8 ppm of diammonium hydrogenphosphate $(NH_4)_2HPO_4$ (3 ppm as calculated in terms of phosphorus), based on the ethylene glycol, was added and the reaction temperature was set at 505° C.

As a result, the conversion of ethylene glycol, glyoxal selectivity and glycolaldehyde selectivity were 100%, 70.2% and 2.9%, respectively.

EXAMPLE 9

A reaction was effected in the same manner as in Example 2 except that 19.1 ppm of triethylphosphine (5 ppm as calculated in terms of phosphorus), based on the ethylene glycol, was added and the reaction temperature was set at 505° C.

As a result, the conversion of ethylene glycol, glyoxal selectivity and glycolaldehyde selectivity were 100%, 70.7% and 3.3%, respectively.

We claim:

1. A process for preparing glyoxal by subjecting ethylene glycol to gas-phase oxidation, which process comprises bringing the ethylene glycol and a gas containing molecular oxygen into contact at a temperture in the range of 450°–650° C. with a silver catalyst in the simultaneous feeding of one or more phosphorus compounds in a vapor phase to effect the oxidation of the ethylene glycol, the amount of the molecular oxygen used is 0.7–2.0 moles per mole of the ethylene glycol and the amount of the fed phosphorus compounds is 50 ppm or less as calculated in terms of phosphorus relative to the ethylene glycol.

2. A process according to claim 1, wherein the silver catalyst has particle sizes of about 2.5 mm or smaller.

3. A process according to claim 1, wherein at least part of the silver catalyst is fine silver powder having particle sizes of $1 \times 10^{-3}$ mm or smaller.

4. A process according to claim 1, wherein the phosphorus compounds are fed in an amount of 1–50 ppm as calculated in terms of phosphorus relative to the ethylene glycol.

5. A process according to claim 1, wherein the phosphorus compound is one or more phosphorus compound selected from the group consisting of methyl phosphite, ethyl phosphite, methyl phosphate and ethyl phosphate.

6. A process according to claim 1, wherein 5 or more moles of a diluting inert gas are used per mole of the ethylene glycol.

7. A process according to claim 1, wherein the residence time of the reaction gas in the layer of the silver catalyst is controlled to 0.03 second or less.

8. A process for preparing glyoxal comprising:
    (a) feeding simultaneously in vapor phase to a reactor;
        (i) ethylene glycol;
        (ii) a gas, said gas containing molecular oxygen between 0.7 and 2.0 moles per mole of said ethylene glycol; and
        (iii) at least one phosphorus compound said phosphorus compound being fed in said vapor phase at 50 ppm relative to said ethylene glycol; and
    (b) contacting said ethylene glycol, said gas, and said phosphorus compound with a powdered silver catalyst at a temperature between 450° C. and 650° C., said powder silver catalyst having particle sizes of up to $1 \times 10^{-3}$ mm, whereby said ethylene glycol and said oxygen are converted to glyoxal.

* * * * *